United States Patent [19] [11] 4,355,636
Oetjen et al. [45] Oct. 26, 1982

[54] HUMDIFIER AND HEATER FOR AIR TO BE INHALED FOR CONNECTION TO AN INHALATION CONDUIT OF A RESPIRATOR

[75] Inventors: Georg-Wilhelm Oetjen, Lübeck; Frank Benthin, Lübeck-Hamberge, both of Fed. Rep. of Germany

[73] Assignee: Drägerwerk AG, Fed. Rep. of Germany

[21] Appl. No.: 161,352

[22] Filed: Jun. 20, 1980

[30] Foreign Application Priority Data

Jul. 21, 1979 [DE] Fed. Rep. of Germany ....... 2929706

[51] Int. Cl.³ ............................................. A61M 16/00
[52] U.S. Cl. .......................... 128/204.13; 128/204.17; 165/133; 165/DIG. 10; 261/DIG. 65; 261/104
[58] Field of Search ...................... 128/201.13, 204.15, 128/204.17, 203.26, 203.27; 165/140, 141, DIG. 10, 133; 261/DIG. 65, 104

[56] References Cited

U.S. PATENT DOCUMENTS

| 1,123,201 | 12/1914 | Almirall | 165/140 |
| 2,448,315 | 8/1948 | Kunzog | 165/DIG. 10 |
| 2,670,933 | 3/1954 | Bay | 165/140 |
| 3,170,512 | 2/1965 | Smith | 165/DIG. 10 |
| 3,747,598 | 7/1973 | Cowans | 128/201.13 |
| 4,146,597 | 3/1979 | Eckstein et al. | 128/204.13 |
| 4,155,961 | 5/1979 | Benthin | 128/204.13 |

Primary Examiner—Henry J. Recla
Attorney, Agent, or Firm—McGlew and Tuttle

[57] ABSTRACT

A humidifier and heater for air to be inhaled for connection to an inhalation conduit of a respirator comprises a housing having a bundle of vapor permeable fiber tubes which have evaporation fiber wall surfaces extending therethrough. A packing is arranged adjacent each end of the housing in said tubes and seals the space in the housing around the tubes between the packing. The tubes in the interior of the housing in the space have a coating on their exteriors of at least either copper or silver. Warm water is circulated into the housing in the space around the tubes and the inhalation air is directed through the tubes or vice versa.

3 Claims, 1 Drawing Figure

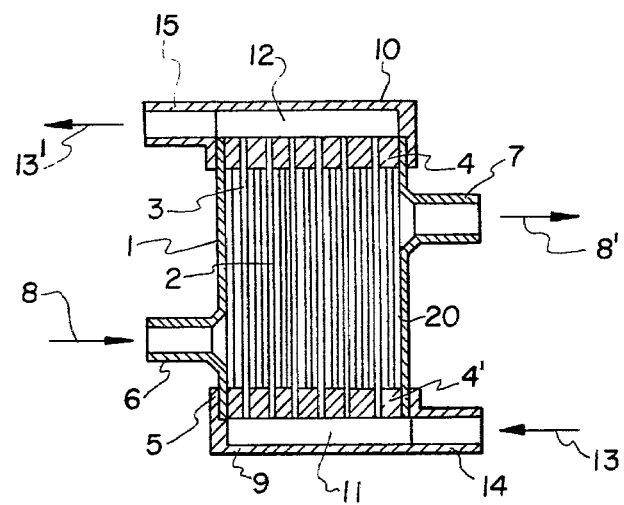

HUMIDIFIER AND HEATER FOR AIR TO BE INHALED FOR CONNECTION TO AN INHALATION CONDUIT OF A RESPIRATOR

FIELD AND BACKGROUND OF THE INVENTION

This invention relates in general to the construction of breathing apparatus and in particular to a new and useful humidifier and heater for air to be inhaled.

In the mechanical respiration of patients by way of intubation, but also in spontaneous breathing of patients with tracheotomy, the air to be inhaled does not pass through the area of throat, nose and pharynx, but passes immediately into the bronchi. Since the area of the throat, nose and pharynx is not contacted with the air to be inhaled, the air to be inhaled connot be sufficiently warmed and moistened. The result is a drying up of the respiratory paths. The thermal balance of the patient is disturbed, and special attention is required for aseptic conditions.

In a known humidifier for air to be inhaled the supply of air to the patient is provided from an air supply apparatus with a wavy tube. Inside of this tube is a folded water conduit inner tube, the connections of which are linked to the water supply. The wall of the water conduit inner tube are water impermeable, but water vapor permeable. The air to be inhaled is conducted through the wavy tube and surrounds the water conduit inner tube. The air is moistened by the water permeating as a vapor. In another embodiment, the tube conducting the air to be inhaled can be installed in a water container hanging around the neck of the user and inserted into the breathing gas connection to the respirator or in the connection directly coming from the atmosphere.

Herein the breathing tube with polytetrafluoroethylene walls, guided in up and down running windings, can be part of the water container. Its inlet can be connected either directly to the atmosphere or with a similarly portable container of liquid oxygen. Its outlet runs to a tracheotomy cannula or to a transnasal catheter.

It is claimed that the water supply is heated by body heat. These known humidifiers for air to be inhaled are very large. A fairly large supply of water is required for sufficient moistening. The heating of the air to be inhaled by transfer of body heat via the water supply appears to be a problem. The maintenance of aseptic conditions during use appears to be impossible. The extension for successive cleaning and disinfection is difficult, if not even unrealizable. (see U.S. Pat. No. 3,871,373).

Another known humidifier for air to be inhaled, which can already be built smaller, allows for a simpler construction of the evaporator unit. The unit can be exchanged after use. However, the loading of the patient with germs by the humidifier for air to be inhaled during use is not prevented. This humidifier for air to be inhaled comprises an exchangeable evaporator unit in a casing, which allows for installation at a desired location directly in the respirator. This evaporator unit comprises a bundle of hollow fibers bent into U-shape through which warm water is conducted. The unit with the hollow fibers is placed in the casing, which is passed by the breathing air to be humidified.

The evaporator unit can be exchanged after each use. The casing, which is complex for providing aseptic conditions, has to be disassembled in individual parts and they have to be sterilized. (German Patent Application Disclosure No. 27 03 892).

SUMMARY OF THE INVENTION

The invention provides a smaller and lighter humidifier and heater for air to be inhaled, which prevents a loading of the patient with germs during use. It is also easy to handle.

In accordance with the invention the humidifier and heater for air to be inhaled for connection to a respirator comprises an intermediate housing casing which has packing at each end through which a bundle of fiber tubes or tubules extend. The space around the tubes and between the packing in the housing defines a space for the passage of air to be humidified by warm water which is circulated passed through one of the tube ends and through the tubes to the opposite end. The housing includes a cover at each end which defines an inflow and outflow passage to the tubes and the intermediate section or part of the housing includes an inlet and an outlet for the circulation of warm water.

The covering of the surfaces contacted by the air to be inhaled with metals represents a substantial advance. The known bactericidal effects of copper and/or silver assure, that exhaled microorganisms cannot multiply or they are killed even under otherwise favorable growth conditions.

The technical construction of the humidifier and heater for air to be inhaled of the present invention is advantageous and simple. It allows a sure covering with the metals and furthermore assembly of the individual parts. These can be produced inexpensively, for example from plastics.

Accordingly it is an object of the invention to provide a humidifier and heater for air to be inhaled for use with a respirator which includes a housing having packing adjacent each end through which ends of a bundle of fiber tubes extend which includes means for circulating warm water over the tubes in the space between the packing and for circulating air to be humidified and heated through the tubes.

A further object of the invention is to provide a humidifier and heater for air to be inhaled which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

The only FIGURE of the drawing is a sectional view of a humidifier and heater for air to be inhaled for connection to an inhalation conduit of a respirator constructed in accordance with the invention.

EMBODIMENT

Referring to the drawings in particular the invention embodied therein comprises a humidifier and heater for air to be inhaled for connection to an inhalation conduit of a respirator which has a line connected into an inlet tube 6 of the humidifier and heater and to an outlet tube 7. The humidifier and heater includes a housing 1 made up of an intermediate case part 5 and end fittings or covers 9 and 10 respectively.

The humidifier and heater for air to be inhaled comprises an evaporator unit 2 located in the housing 1. The unit 2 comprises a bundle of hollow fibers or tubules 3 which are sealed at their ends in packings or seals 4, 4' which hold them in an intermediate housing part or case part 5. The case part 5 is provided at its sides, with respective connecting pipes 6 and 7 for the entrance in the direction of arrow 8 of the breathing air to be humidified and heated which is then delivered outwardly in the direction of arrow 8'. The air surrounds the hollow fiber tubes 3 in a space 20 around the tubules, on its way through the case part 5.

The case part 5 is closed at respective ends with the bottom fitting or plate 9 and a top fitting cover 10. In the evaporator unit 2 they form thereby a water feed space 11 and a water removal space 12. Warm water is fed in the direction of arrow 13 through a connecting pipe 14, and then passes through the hollow fibers 3, which are surrounded by the air to be inhaled in the space 20 and the water leaves the housing 1 through a connecting pipe 15 as shown by arrow 13'. Evaporated water or vapor is transported through the hollow fiber walls and humidifies the air to be inhaled. The heat energy from the warm water heats up the air to be inhaled.

The humidifier and heater for air to be inhaled can be formed for example with interconnected cemented case parts 5, 9 and 10 as a throw away item. Embodiments are possible wherein only the evaporator unit is exchanged.

A practical hollow fiber comprises the permeable membrane, which is held by a supporting construction. The membrane thickness can be from one to a few micrometers and depends on the requirements of the permeation; the thickness of the support construction depends on the mechanical loading.

In accordance with the invention, copper or silver, or both, are placed on the outer surface of the hollow fibers and the inside surfaces of housing 1 which are contacted by the air to be inhaled. The copper and silver may be evaporated into these surfaces in a vacuum or placed thereon by sputtering. This metallic application, as noted hereinbefore, provides a bactericidal effect.

While a specific embodiment of the invention has been shown and described in detail to illustrate the application of the principles of the invention, it will be understood that the invention may be embodied otherwise without departing from such principles.

What is claimed is:

1. A respirator humidifier and heater for air to be inhaled for connection to an inhalation conduit of a respirator, comprising a housing having a bundle of vapor permeable fiber tubes with evaporation fiber wall surfaces extending therethrough, a packing adjacent each end of said tubes sealing a space in said housing around said tubes between said packings, said tubes and the interior of said housing having a thin porous coating on their exterior surfaces of at least one of copper and silver, means for passing inhalation air into the housing in the space around said tubes between said packings, means for circulating warm water through said tubes, wherein said at least one of copper and silver are evaporated onto the surfaces in a vacuum.

2. A respirator humidifier and heater for air to be inhaled for connection to an inhalation conduit of a respirator, comprising a housing having a bundle of vapor permeable fiber tubes with evaporation fiber wall surfaces extending therethrough, a packing adjacent each end of said tubes sealing a space in said housing around said tubes between said packings, said tubes and the interior of said housing having a thin porous coating on their exterior surfaces of at least one of copper and silver, means for passing inhalation air into the housing in the space around said tubes between said packings, means for circulating warm water through said tubes, wherein said at least one of copper and silver are applied to the surfaces by sputtering.

3. A humidifier according to claim 1 or 2, wherein said housing includes an intermediate case part carrying said bundle of tubes and an end piece fitted to said casing part enclosing each end and providing a passage for the inlet and outlet of the air to be inhaled.

* * * * *